United States Patent [19]

Gervais

[11] Patent Number: 4,908,449
[45] Date of Patent: Mar. 13, 1990

[54] PROCESS FOR PREPARING N-METHYL DERIVATIVES OF LYSERGOL AND 10α-METHOXYLUMILYSERGOL

[75] Inventor: Christian Gervais, Villeurbanne, France

[73] Assignee: Rhone-Poulenc Sante, Antony, France

[21] Appl. No.: 329,387

[22] Filed: Mar. 27, 1989

[51] Int. Cl.$^4$ .................................................. C07D 457/02
[52] U.S. Cl. ........................................ 546/67; 546/68; 546/69
[58] Field of Search .............................. 546/67, 68, 69

[56] References Cited

U.S. PATENT DOCUMENTS

| | | | |
|---|---|---|---|
| 3,183,234 | 5/1965 | Garbrecht et al. | 546/68 |
| 3,228,943 | 1/1966 | Bernardi et al. | 546/68 |
| 3,580,916 | 5/1971 | Garbrecht | 546/69 |
| 3,879,554 | 4/1975 | Temperilli | 546/68 |
| 4,232,157 | 11/1980 | Enrico | 546/68 |
| 4,734,501 | 3/1988 | Marzoni | 546/67 |
| 4,754,037 | 6/1988 | Gervais | 546/67 |
| 4,772,709 | 9/1988 | Marzoni | 546/67 |

FOREIGN PATENT DOCUMENTS 2616788  12/1988  France .................................. 546/67

*Primary Examiner*—Mukund J. Shah
*Assistant Examiner*—Cecilia Shen
*Attorney, Agent, or Firm*—Stevens, Davis, Miller & Mosher

[57] ABSTRACT

A process for preparing 1-methyllysergol or 10α-methoxy-1-methyllumilysergol, which comprises adding a base, which is an alkali metal hydride or alcoholate, to a solution of lyergol or 10α-methoxylumilysergol in a polar aprotic solvent in such a way that the molecular ratio between the base and the lysergol or 10α-methoxylumilysergol remains less than 0.5:1, and then adding a methylating agent which is methyl iodide, methyl sulphate or trimethylsulphonium iodide.

1-methyllysergol and 10α-methoxy-1-methyllysergol are useful intermediates in the synthesis of pharmacological compounds.

3 Claims, No Drawings

PROCESS FOR PREPARING N-METHYL DERIVATIVES OF LYSERGOL AND 10α-METHOXYLUMILYSERGOL

The present invention relates to a process for preparing 1-methyllysergol and 10α-methoxy-1-methyl-lumilysergol, which are useful intermediates in the synthesis of pharmacological compounds described in U.S. Pat. No. 3,228,943.

It is known, in particular from French Pat. No. 2,421,901, to prepare 10α-methoxy-1-methyllumilysergol by the action of methyl iodide in the presence of potassium hydroxide, working in dimethyl sulphoxide. However, under these conditions, competition exists between the methylation of the indole nitrogen atom and the primary alcohol group.

The present invention provides a process for the selective methylation of lysergol or 10α-methoxylumilysergol which comprises adding a base, which is an alkali metal hydride or alcoholate, to a solution of lysergol or 10α-methoxylumilysergol in a polar aprotic solvent in such a way that the molecular ratio between the base and the lysergol or 10α-methoxylumilysergol remains less than 0.5:1, and then adding a methylating agent which is methyl iodide, methyl sulphate or trimethylsulphonium iodide.

It is especially advantageous to add the methylating agent at a rate such that it is not in excess with respect to the base to avoid the formation of quaternary ammonium derivatives.

The polar aprotic solvents which are especially suitable in the present invention are N-methylpyrrolidone, hexamethylophosphorotriamide, tetramethylurea, dimethylformamide and dimethylacetamide.

The selectivity of the reaction is favoured if the base used is sodium hydride or potassium hydride.

In general, the process according to the invention is carried out at a temperature of from 0° to 60° C.

The 1-methyllysergol or 10α-methoxy-1-methyl-lumilysergol obtained by carrying out the process can be separated and isolated according to customary methods.

The examples which follow show how the invention can be put into practice.

EXAMPLE 1

10α-Methoxylumilysergol (286 mg; 1 mmol) was dissolved in N-methypyrrolidone (6 cc), and sodium hydride (45.6 mg; 1.9 mmol) was then added in several portions with evolution of hydrogen.

A 9% (by volume) solution of methyl iodide in N-methylpyrrolidone was added, at a temperature of about 20° C., to the stirred suspension, at a rate of 0.25 mmol/hour.

The results obtained are collated in the following table:

| Methyl iodide (mmol) | Degree of conversion of 10α-methoxylumily-sergol % | Yield of 10α-methoxy-1-methyl-lumilysergol % | Yield of O—to and N—methylated product % |
|---|---|---|---|
| 1 | 86.8 | 79.1 | 0.9 |
| 1.1 | 93 | 83.4 | 1.35 |
| 1.15 | 95.2 | 85.0 | 1.7 |
| 1.20 | 97.4 | 85.1 | 2.2 |
| 1.25 | 98.5 | 85.0 | 2.6 |
| 1.35 | 99.3 | 82.5 | 2.9 |

EXAMPLE 2

Lysergol (2.134 g; 8 mmol) and potassium tert-butylate (0.19 g; 1.7 mmol) were dissolved in hexamethylphosphorotriamide (20 cc). Two solutions were then added simultaneously while the mixture was stirred:

a solution of methyl iodide in hexamethylphosphorotriamide (2 mol/liter) at a rate of 8 mmol/hour;

a solution of potassium tert-butylate in hexamethylphosphorotriamide (1.06 mol/liter) at a rate of 7.2 mmol/hour.

The results obtained are collated in the following table. The degree of conversion of the lysergol was measured by determining the amount of lysergol remaining in the reaction mixture. The yield of 1-methyl-lysergol was measured as the weight percentage of 1-methyl-lysergol in the reaction mixture based on the total weight of engoline derivatives present in the reaction mixture.

| Hours | Excess Base Initial Lysergol (I) | Potassium Tert-butylate (Total) m.moles | Methyl Iodide (Total) m.moles | Degree of Conversion of lysergol % | Yield of 1-methyl lysergol % | Yield of O— and N—dimethylated product % |
|---|---|---|---|---|---|---|
| 0 | 0.21 | 1.7 | 0 | 0 | 0 | 0 |
| 0.5 | 0.16 | 5.3 | 4 | 39.5 | 39.5 | 0 |
| 1 | 0.11 | 8.9 | 8 | 78 | 80.5 | about 1.6 |
| 1.1 | 0.10 | 9.6 | 8.8 | 87 | 86 | about 1.5 |
| 1.2 | 0.09 | 10.3 | 9.6 | 95 | 93 | about 1.7 |
| 1.24 | 0.09 | 10.6 | 9.92 | 96.5 | 94 | about 2.4 |
| 1.275 | 0.09 | 10.9 | 10.20 | 97.5 | 94 | about 3.5 |
| 1.3 | 0.09 | 11.1 | 10.40 | 99 | 94 | about 4.4 | i.e. total potassium tert-butylate-total methyl iodide total lysergol

COMPARATIVE EXAMPLES 3

Lysergol (1.017 g; 4 mmol) was anionized for 1 hour using anhydrous powdered sodium hydroxide (0.64 g; 16 mmol) in dry hexamethylphosphorotriamide (15 cc).

Undiluted methyl iodide was then added at a flow rate of 1.2 mmol/hour using a proportioning pump.

The results are collated in the following table:

| Hours | Excess Base Initial Lysergol (I) | Potassium Tert-butylate (Total) m.moles | Methyl Iodide (Total) m.moles | Degree of Conversion of lysergol % | Yield of 1-methyl lysergol % | Yield of O— and N—dimethylated product % |
|---|---|---|---|---|---|---|
| 0 | 4 | 16 | 0 | 0 | 0 | 0 |
| 3.8 | 2.85 | 16 | 4.6 | 91.2 | 84.0 | 5.3 |
| 4 | 2.80 | 16 | 4.8 | 92.8 | 84.6 | 5.7 |
| 4.2 | 2.75 | 16 | 5 | 93.1 | 85.4 | 6.2 |
| 4.3 | 2.7 | 16 | 5.2 | 93.9 | 85.0 | 6.4 |
| 4.5 | 2.65 | 16 | 5.4 | 94.3 | 84.4 | 6.6 |
| 4.8 | 2.56 | 16 | 5.76 | 94.7 | 84.0 | 6.8 |

This experiment shows that the maximum yield of 1-methyllysergol is 85%, whereas the yield in Example 2 is 94% for similar mole ratios of total amount of methyl iodide added to lysergol. Additionally it shows that the yield of unwanted O- and N-methylated by-products ranges from 5.3% to 6.8% whereas the yield in Example 2 is much smaller.

I claim:

1. A process for preparing 1-methyllysergol, which comprises adding a base, which is an alkali metal hydride or alcoholate, to a solution of lysergol in a polar aprotic solvent in such a way that the molecular ratio between the base and the lysergol remains less than 0.5:1 throughout the reaction, and then adding a methylating agent which is methyl iodide, methyl sulphate or trimethylsulphonium iodide.

2. A process according to claim 1, wherein the polar aprotic solvent is N-methylpyrrolidone, hexamethylphosphorotriamide, tetramethylurea, dimethylformamide or dimethylacetamide.

3. A process according to claim 1, wherein the methylating agent is added at a rate such that it is not in excess with respect to the base.

* * * * *

UNITED STATES PATENT AND TRADEMARK OFFICE
CERTIFICATE OF CORRECTION

PATENT NO. : 4,908,449
DATED : March 13, 1990
INVENTOR(S) : Christian GERVAIS

It is certified that error appears in the above-identified patent and that said Letters Patent is hereby corrected as shown below:

In the heading, insert:

Related U. S. Application Data

[63] Continuation-in-Part of Serial No. 06/884,044, filed July 10, 1986 and now abandoned.

Foreign Application Priority Data

[30] July 11, 1985 [FR] France ... 85-10621

In column 1 following the title of the invention, insert: --This application is a Continuation-in-Part of application Serial No. 884,044, filed July 10, 1986 and now abandoned.

Signed and Sealed this

Fifth Day of March, 1991

Attest:

HARRY F. MANBECK, JR.

Attesting Officer  Commissioner of Patents and Trademarks